United States Patent [19]

Weissman

[11] 4,155,162
[45] May 22, 1979

[54] DENTAL ANCHOR MAGAZINE

[75] Inventor: Bernard Weissman, New York, N.Y.

[73] Assignee: IPCO Hospital Supply Corporation, White Plains, N.Y.

[21] Appl. No.: 834,178

[22] Filed: Sep. 19, 1977

Related U.S. Application Data

[63] Continuation-in-part of Ser. No. 669,688, Mar. 23, 1976, Pat. No. 4,053,982.

[51] Int. Cl.² .............................................. A61K 5/01
[52] U.S. Cl. .......................................... 32/15; 81/71; 81/121 A; 81/3 R; 279/93
[58] Field of Search ................... 32/15, 2, 10 R, 10 A; 29/809, 811; 81/3 R, 121 A, 121 B, 119, 71, 57.23, 177.9; 85/61, 9 R; 403/82, 83, 84, 93, 21, 215; 206/379, 377; 279/93, 94, 76, 77, 78, 79, 80, 81, 82, 83, 84, 85, 86, 87

[56] References Cited

U.S. PATENT DOCUMENTS

| | | | |
|---|---|---|---|
| 1,358,687 | 11/1920 | Lyon | 85/9 R |
| 1,575,753 | 3/1926 | Gibson | 29/811 |
| 1,990,928 | 2/1935 | Bodendieck | 81/121 A |
| 2,719,042 | 9/1955 | Espy | 81/71 |
| 2,726,091 | 12/1955 | Topar | 81/71 |
| 2,851,915 | 9/1958 | Martinez | 279/93 |
| 3,113,479 | 12/1963 | Swingle | 81/71 |
| 3,228,269 | 1/1966 | Heyer | 81/3 R |
| 3,675,328 | 7/1972 | Weissman | 32/15 |

*Primary Examiner*—Louis G. Mancene
*Assistant Examiner*—Michael J. Foycik, Jr.
*Attorney, Agent, or Firm*—Friedman, Goodman & Teitelbaum

[57] ABSTRACT

A dental anchor magazine housing a dental anchor therein is disclosed, where the dental anchor is for anchoring a superstructure to a tooth. The dental anchor includes threaded sections and an L-shaped manipulating end section joined together by frangible reduced thickness portions. The dental anchor magazine includes a body member having a conical front end, and a square shaped rear end for rotating the magazine about its longitudinal axis. A centrally located passageway extends longitudinally through the body member to receive the dental anchor therein. A slot extends transversely through the body member into communication with the passageway for longitudinal movement of the manipulating section of the dental anchor therein. A pair of notches are provided in the wall of the slot for receiving the manipulating section of the dental anchor to prevent movement of the dental anchor towards the rear end when the forward end of the dental anchor is being initially threaded into a channel of a tooth, where the forward end of the dental anchor extends outwardly from the front end of the body member when being threaded into the channel. The square shaped rear end of the body member is engageably received in either a manual holder for manual rotation thereof or a handpiece holder for power rotation thereof by a dental handpiece. Both the manual holder and the handpiece holder include a pin member for advancing the manipulating section to a first one of the notches.

20 Claims, 10 Drawing Figures

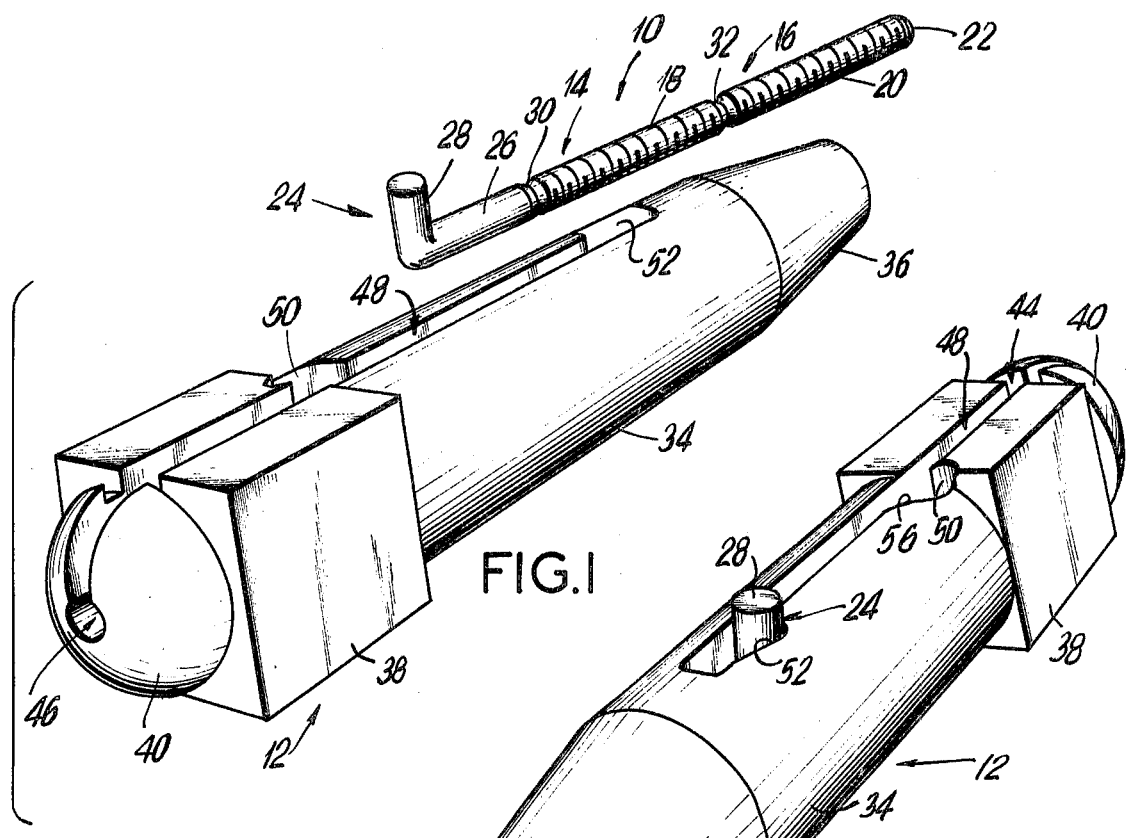
FIG. 1
FIG. 2
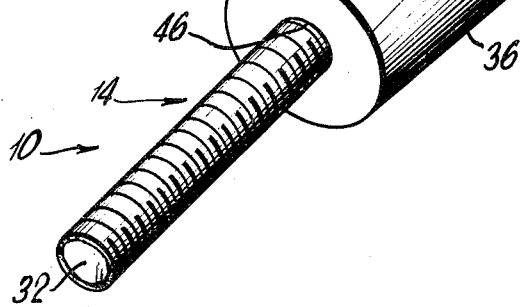
FIG. 3
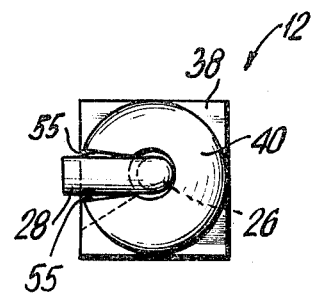
FIG. 4

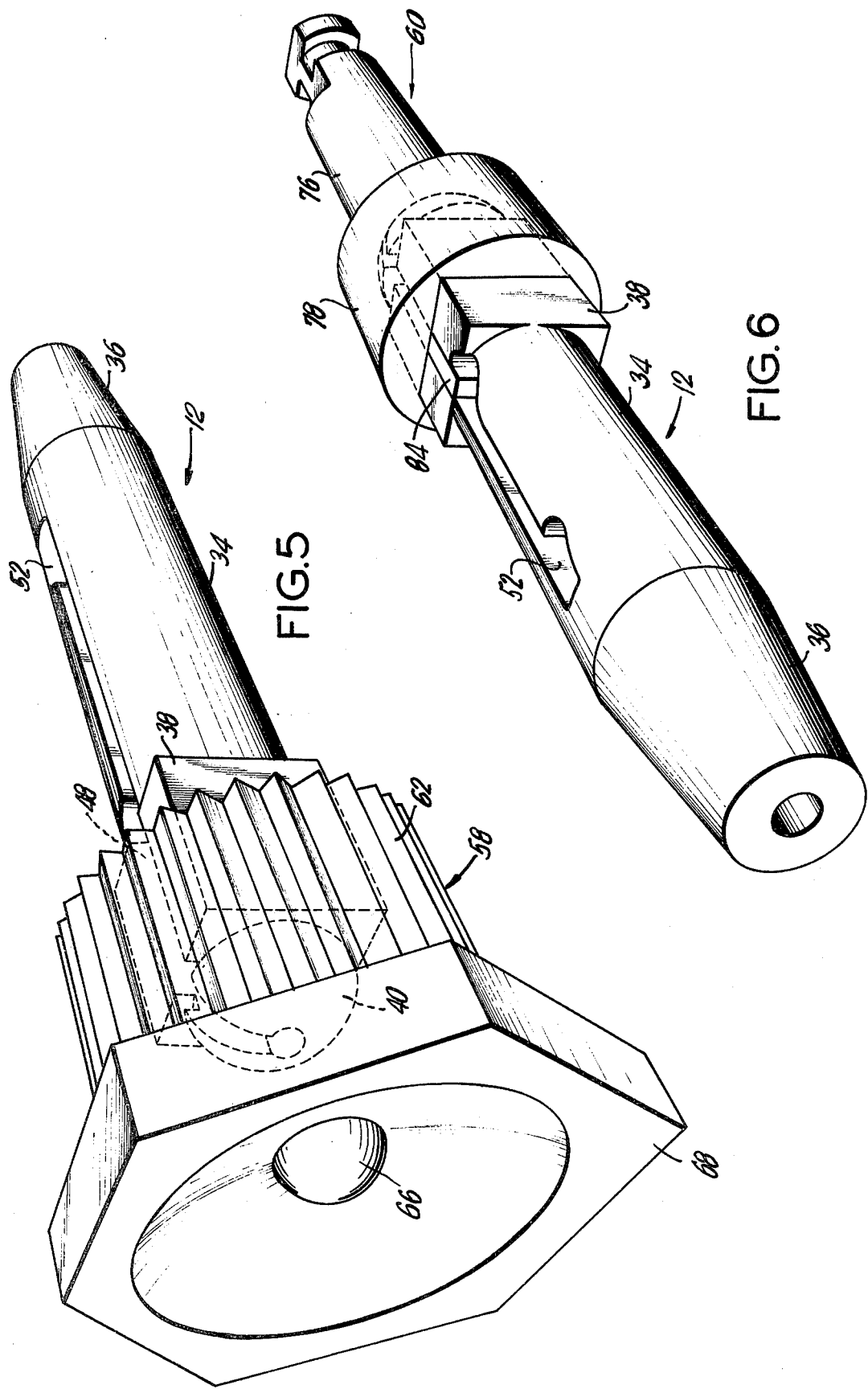

DENTAL ANCHOR MAGAZINE

CROSS REFERENCE TO RELATED APPLICATION

The present application is a continuation-in-part application of U.S. application Ser. No. 669,688 filed Mar. 23, 1976, for a DENTAL ANCHOR now U.S. Pat. No. 4,053,982.

BACKGROUND OF THE INVENTION

The present invention relates to dentistry in general, and more particularly to an improvement in apparatus for building superstructures on broken or undermined dentition, the apparatus being a dental anchor magazine housing a dental anchor.

Prior art apparatus for anchoring a superstructure to an understructure of a tooth requires drilling a number of channels into the tooth or understructure, where anchoring rods are then inserted into the channels and are allowed to protrude above the understructure so that the protruding portions thereof serve as means for anchoring the superstructure. It is noted, that these anchoring rods are extremely small, being on the order of 0.03" in diameter and approximately 0.2" in length.

Because of the relatively small size of the anchoring rods, and because of the limited working areas, a chuck attachment or a coupling tool is used by the dentist to hold the anchoring rods when being iserted into the channels. The chuck attachment or coupling tool is disclosed in my co-pending U.S. Pat. application Ser. No. 669,688, and also in my U.S. Pat. No. 3,675,328, to which reference may be made. It is noted, that each of the anchoring rods must be inserted by the dentist into the socket of the chuck attachment or coupling tool, which is time consuming. Only the manipulating portion of the anchoring rod is received in the chuck attachment or coupling tool, so that only a limited coupling engagement is provided therebetween. Furthermore, the prior art anchoring rods mentioned above are useless without the chuck attachment or coupling tool, which may easily be lost or misplaced by the dentist, thereby causing further delay in the replacement thereof.

SUMMARY OF THE INVENTION

Accordingly, it is an object of the present invention to provide improved means for building a superstructure on broken or undermined dentition.

Another object of the present invention is to provide improved means for positively holding the anchoring rods used for anchoring a superstructure to an understructure of a tooth.

A further object of the present invention is to provide a dental anchor magazine for housing anchoring rods.

Yet another object of the present invention is to provide a dental anchor magazine housing a dental anchor having sections that are readily severable from one another to permit successive respective insertions into channels formed in the understructure of a tooth.

Yet another object of the present invention is to provide a dental anchor magazine, housing a dental anchor therein, which is readily engageable in either a manual holder for manual rotation thereof or a handpiece holder for power rotation thereof by a dental handpiece, in order to anchor the dental anchor housed in the dental anchor magazine.

These objects are achieved in accordance with the present invention, wherein each dental anchor magazine houses a dental anchor therein, the dental anchor being for anchoring a superstructure to a tooth. The dental anchor includes at least one or more threaded sections and one L-shaped manipulating end section joined together by frangible reduced thickness portions so that these sections can be severed after being threaded into a channel in the tooth. The manipulating end section includes a projecting torque transferring portion disposed perpendicular, or at my suitable angle, to the longitudinal axis of the dental anchor.

The dental anchor magazine includes a body member having a conical front end, and a square shaped rear end for rotating the magazine about its longitudinal axis which coincides with the longitudinal axis of the dental anchor. A centrally located passageway extends along the longitudinal axis through the body member, being dimensioned to receive the dental anchor therein. Additionally, a slot extends transversely from an outer surface through the body member into communication with the passageway to permit longitudinal movement of the torque transferring portion of the dental anchor through the body member. The slot extends longitudinally from the rear end of the body member to a spaced distance from the conical front end, so that the torque transferring portion of the dental anchor can be positioned through the rear end with the front end of the body member preventing the dental anchor from moving transversely out of the passageway when the dental anchor is extended through the front end.

In order to prevent the movement of the torque transferring portion along the slot towards the rear end of the body member when the forward end of the dental anchor is being initially threaded into a channel of a tooth, a pair of notches are provided in the wall of the slot for receiving the torque transferring portion, it being noted that the front end of the dental anchor extends outwardly from the front end of the body member when being threaded into the channel. The square shaped rear end of the body member is engageably received in either a manual holder to provide manual rotation thereof, or a handpiece holder to provide power rotation thereof by a dental handpiece. Both the manual holder and the handpiece holder include a pin member for advancing the torque transferring portion from the rear end surface of the body member to a first one of the notches.

Thus, after a first threaded section most remote from the manipulating end section has been sufficiently threaded into one channel in the tooth, this first threaded section is snapped off at its frangible portion to thereby leave a second threaded section most proximate the manipulating end section in tact with the manipulating end section. The second threaded section of the dental anchor is still retained in the dental anchor magazine, where the torque transferring portion is moved to the second notch remote from the rear end, so that the second threaded section may be immediately inserted into a successive channel in the tooth without reloading the dental manual holder or handpiece holder. After the second threaded section has been sufficiently threaded into the second channel, the manipulating end portion is snapped off at the second frangible portion, whereby the dental anchor magazine containing the severed manipulating end portion may be disposed of, being of the throw-away type.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 is an exploded rear perspective view illustrating the dental anchor and the dental anchor magazine of the present invention;

FIG. 2 is a front perspective view illustrating the dental anchor magazine housing the dental anchor;

FIG. 3 is an elevational view illustrating the slot in the dental anchor magazine and the torque transferring portion of the dental anchor associated therewith;

FIG. 4 is a rear end elevational view of the dental anchor magazine and dental anchor shown in FIG. 3;

FIG. 5 is a rear perspective view illustrating a manual holder attached to the dental anchor magazine;

FIG. 6 is a front perspective view illustrating a handpiece holder attached to the dental anchor magazine;

In the various figures of the drawings like reference characters designate like parts.

DETAILED DESCRIPTION OF THE PREFERRED EMBODIMENT

Figure 7:
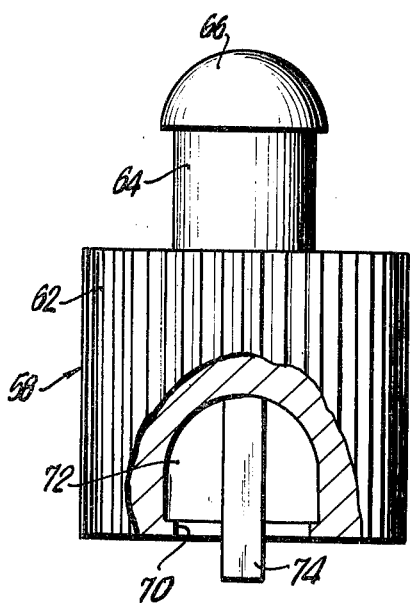
FIG. 7 is a fragmentary, elevational view illustrating the manual holder of FIG. 5, with the finger positioner removed.

FIG. 1 shows a dental anchor 10 and a magazine 12 according to the present invention. The dental anchor 10 includes a one piece elongated body having first and second coaxial sections 14 and 16, where the number of sections may be varied for particular requirements. Threads 18 and 20 are formed on at least a portion of each of the sections 14, 16 respectively, with the end of section 16 terminating in a bevelled or chamfered end 22. A manipulating section 24 is formed integrally with the end of the section 14 that is remote from the end 22 of the section 16. The manipulating section 24 includes a cylindrical guide portion 26 disposed along the longitudinal axis of the dental anchor and connected to the section 14, and a cylindrical torque transferring portion 28 that is integral with the guide portion 26 and preferably perpendicular thereto. It is noted that the portion 28 may be disposed at any suitable angle to the longitudinal axis of the dental anchor.

The dental anchor 10 also includes a first frangible reduced thickness portion 30 between the section 14 and the guide portion 26, and a second frangible reduced thickness portion 32 between the sections 14 and 16. The dimensions of the two frangible reduced thickness portions are selected such that the thickness of the first portion 30 is greater than that of the second portion 32 in order that the elongated body will fracture first at the second frangible portion 32 when being inserted into a channel formed in the understructure of a tooth or dentition, as set forth in my above-mentioned patent and application.

The magazine 12, as shown in FIGS. 1-4, includes a cylindrical body member 34 having a tapered or conical end portion 36. A square shaped block member 38 is integrally connected to the opposite end of the body member 34 and has a rounded or arcuate end 40 connected thereto by a reduced cylindrical portion 42 to provide a groove or undercut 44 between the rounded end 40 and the block member 38.

A centrally located bore or passageway 46 is disposed along the longitudinal axis and extends completely through the magazine 12 for receiving the dental anchor 10. A slot 48 extends through one side of the magazine 12 into communication with the bore 46, where the slot 48 extends longitudinally across the end 40, the reduced portion 42, the block member 38 and a major portion of the body member 34, as shown in the drawings, where the slot 48 terminates before the conical end portion 36. Additionally, a first receiving notch 50 and a second receiving notch 52 are formed on the same side of the slot 48 and extend downwardly into communication with the bore 46. It is noted, that the wall of the slot 48 may be scalloped at 54 between the notch 50 and 52 to provide alternate positions for the torque transferring portion 28, in a manner set forth below. Additionally, the side walls 55 of the slot 48 are tapered or inclined outwardly, as best shown in FIG. 4, so that the torque transferring portion 28 may free pass therethrough.

In assembly, the anchor end 22 is inserted into the rear end of bore 46 at the rounded end 40, and the dental anchor 10 is moved longitudinally into the magazine 12 until the torque transferring portion 28 is disposed in alignment in the slot 48 in the rounded end 40 as shown in FIG. 3, whereby the tip 22 is now disposed at the end of the conical portion 36, where the conical portion 36 prevents the dental anchor 10 from moving transversely out of the bore 46. In use, the torque transferring portion 28 is moved inwardly to the first notch 50, where clockwise rotation of the magazine 12, as shown in FIG. 4, will lock the torque transferring portion 28 in the notch 50 for rotation therewith, whereby the anchor 10 cannot move longitudinally towards the rear or rounded end 40 of the magazine 12 when being threaded into the channel of the tooth or dentition. However, a sloped or inclined wall 56 of the notch 50 allows the torque transferring portion 28 of the dental anchor 10 to move in a forward direction towards the conical portion 36 as the dental anchor 10 is being threaded, where the torque transferring portion 28 moves into the slot 48 between the notches 50 and 52 and is engaged in one of the scallops 54 for alternate positioning thereof.

Once the section 16 of the anchor 10 is seated in the channel of the tooth, further rotation of the magazine 12 will cause the more reduced section 32 to break off, where the rear portion of the section 16 will now protrude from the tooth as desired. The torque transferring portion 28 is now positioned in or moved to the notch 50 so that the section 14 of the anchor 10 protrudes from the conical portion 36 as shown in FIG. 2, whereby the section 14 is now ready to be threaded into a second channel in the tooth, in the same manner as mentioned above. Here again, once the section 14 is seated in the second channel in the tooth, the reduced portion 30 will break off so that the rear portion of section 14 also protrudes from the tooth as desired. Thus, the magazine 12 of the present invention allows easy insertion of the threaded sections into the channels of the tooth or teeth.

FIG. 5 shows a manual holder 58 attached to the magazine 12 for manual rotation thereof, and FIG. 6 shows a handpiece holder 60 which is insertable into a conventional dental handpiece for mechanical or power rotation thereof.

Figure 8:
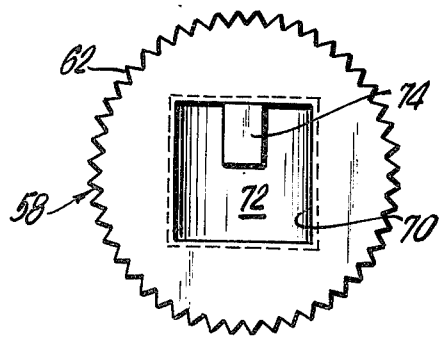
FIG. 8 is a front elevational view of the manual holder shown in FIG. 7.

As shown in FIGS. 5, 7 and 8, the manual holder 58 includes a cylindrical body member 62, which is preferably serrated or knurled, as shown in FIG. 5, for finger gripping thereof. A pin 64 with an enlarged arcuate head 66 extends centrally out from the rear of the body member 62 for rotatably holding a finger positioner 68 on the rear of the body member 62 as shown in FIG. 5. The front portion of the body member 62 has a rectangular opening 70 communicating with a cavity or socket 72 formed therein and having an arcuate rear wall. A rectangular shaped pin or tongue 74 extends from the rear wall of the socket 72 and projects out through the opening 70 as best shown in FIG. 7.

As shown in FIG. 5, the rear portion of the magazine 12 is snapped through the opening 70 into the socket 72 of the holder 58, so that the rounded end 40 abuts against the rear wall of the socket 72 and the pin 74 extends through the slot 48, with the square opening 70 being positioned about the block member 38, whereby rotation of the holder 58 causes the magazine 12 to rotate in the same direction therewith. It is noted, that the pin 74 functions to longitudinally move the torque transferring portion 28 of the anchor 10 from its rear position shown in FIG. 3 into an aligned position with the notch 50, where the pin 74 is lengthwise dimensioned for this purpose.

Figure 9:
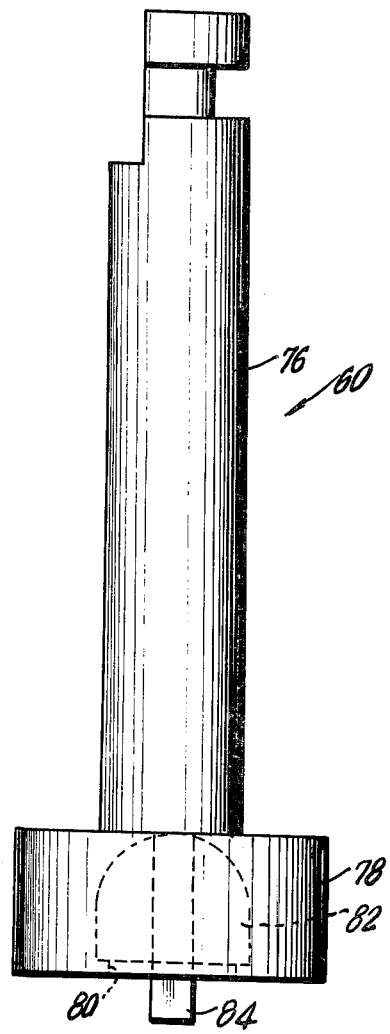
FIG. 9 is an elevational view illustrating the handpiece holder of FIG. 6.
Figure 10:
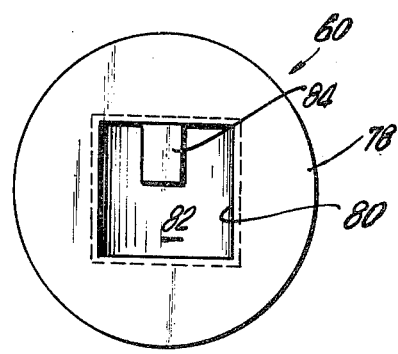
FIG. 10 is a front elevational view of the handpiece holder shown in FIG. 9.

As shown in FIGS. 6, 9 and 10, the handpiece holder 60 includes a conventional cylindrical rear portion 76 adapted to be inserted into a conventional dental handpiece (not shown) in a manner well known in the art. An enlarged cylindrical front end member 78 is integrally connected to the rear portion 76. The front end member 78 is similar to and functions in the same manner as the body member 62 of the manual holder 58. Accordingly, the front face of the front end member 78 has a rectangular opening 80 communicating with a cavity or socket 82 formed therein and having an arcuate rear wall. A rectangular shaped pin or tongue 84 extends from the rear wall of the socket 82 and projects out through the opening 80 as best shown in FIG. 9.

As shown in FIG. 6, the rear portion of the magazine 12 is snapped through the opening 80 into the socket 82 of the handpiece holder 60, so that the rounded end 40 rests against the rear wall of the socket 82 and the pin 84 extends through the slot 48, with the square opening 80 being positioned about the block member 38, whereby rotation of the handpiece holder 60 causes the magazine 12 to rotate in the same direction therewith. Again it is noted, that the pin 84 functions to longitudinally move the torque transferring portion 28 of the anchor 10 from its rear position shown in FIG. 3 into an aligned position with the notch 50, where the pin 84 is lengthwise dimensioned the same as pin 74 for this above mentioned purpose.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental anchor magazine for housing a dental anchor having an outwardly extending torque transferring portion thereon, said magazine comprising:

a body member having a front end portion and an opposite rear end portion, said rear end portion including engageable means for rotating said body member about its longitudinal axis;

passageway means extending longitudinally through said body member from a front end face of said front end portion to a rear end face of said rear end portion for receiving the dental anchor, said passageway means being centrally located through said body member to coincide with the longitudinal axis of said body member;

slot means extending transversely from an outer surface of said body member into communication with said passageway means for longitudinal movement of the torque transferring portion of the dental anchor therein;

notch means provided in a wall of said slot means for receiving the torque transferring portion of the dental anchor to prevent movement of the dental anchor towards said rear end face of said rear end portion when a forward end of the dental anchor is being initially threaded into a channel of a tooth, where the forward end of the dental anchor extends outwardly from said front end face of said front end portion when being threaded into the channel; and said slot means extending longitudinally at least from said notch means through said rear end portion to permit the torque transferring portion of the dental anchor to be positioned through the rear end portion into said notch means.

2. A dental anchor magazine according to claim 1, wherein said notch means includes two spaced apart notches in said wall of said slot means, whereby the torque transferring portion of the dental anchor is first received in one of said two notches closer to said rear end portion, and then the torque transferring portion is moved along said slot means to the other notch.

3. A dental anchor magazine according to claim 2, wherein said one notch has an inclined wall in a direction of said other notch to allow the torque transferring portion to move out of said one notch in the direction of said other notch.

4. A dental anchor magazine according to claim 2, wherein a portion of said wall of said slot means is scalloped between said one notch and said other notch to provide alternate positions for the torque transferring portion of the dental anchor.

5. A dental anchor magazine according to claim 1, wherein said front end portion has a conical configuration, said slot means being spaced from said conical configuration, whereby said conical configuration prevents the dental anchor from moving transversely out of said passageway means when the dental anchor extends through said front end portion.

6. A dental anchor magazine according to claim 1, wherein said engageable means includes a square shaped section on said rear end portion.

7. A dental anchor magazine according to claim 1 including a manual holder for manual rotation of said body member, said manual holder being provided with means for engageably receiving said engageable means of said rear end portion.

8. A dental anchor magazine according to claim 7, wherein said manual holder is provided with pin means for advancing the torque transferring portion of the dental anchor to said notch means.

9. A dental anchor magazine according to claim 1 including a handpiece holder for power rotation of said body member by a dental handpiece, said handpiece holder being provided with means for engageably receiving said engageable means of said rear end portion.

10. A dental anchor magazine according to claim 9, wherein said handpiece holder is provided with pin means for advancing the torque transferring portion of the dental anchor to said notch means.

11. A combination of a dental anchor and a dental anchor magazine for housing said dental anchor, said combination comprising:
(a) said dental anchor including:
(1) at least one threaded section and one manipulating end section disposed along a longitudinal axis of said dental anchor and joined together by a frangible reduced thickness portion so that these sections can be severed after being threaded into a channel in a tooth;
(2) said manipulating end section including a projecting torque transferring portion extending at an angle to the longitudinal axis of said dental anchor;
(b) said dental anchor magazine including:
(1) a body member having a front end portion and an opposite rear end portion, said rear end portion including engageable means for rotating said body member about its longitudinal axis;
(2) passageway means extending longitudinally through said body member from a front end face of said front end portion to a rear end face of said rear end portion for receiving said dental anchor therein, said passageway means being centrally located through said body member to coincide with the longitudinal axis of said body member;
(3) slot means extending transversely from an outer surface of said body member into communication with said passageway means for longitudinal movement of said torque transferring portion of the dental anchor therein;
(4) notch means provided in a wall of said slot means for receiving said torque transferring portion of the dental anchor to prevent movement of the dental anchor towards said rear end face of said rear end portion when a forward end of said threaded section of the dental anchor is being initially threaded into the channel of the tooth, said forward end of said threaded section of the dental anchor extending outwardly from said front end face of said front end portion when being threaded into the channel; and
(5) said slot means extending longitudinally at least from said notch means through said rear end portion to permit said torque transferring portion of the dental anchor to be positioned through the rear end portion into said notch means.

12. A combination according to claim 11, wherein said notch means includes two spaced apart notches in said wall of said slot means, said torque transferring portion of the dental anchor being first received in one of said two notches closer to said rear end portion, and then said torque transferring portion being moved along said slot means to the other notch.

13. A combination according to claim 12, wherein said one notch has an inclined wall in a direction of said other notch to allow said torque transferring portion to move out of said one notch in the direction of said other notch.

14. A combination according to claim 12, wherein a portion of said wall of said slot means is scalloped between said one notch and said other notch to provide alternate positions for said torque transferring portion of the dental anchor.

15. A combination according to claim 11, wherein said front end portion has a conical configuration, said slot means being spaced from said conical configuration, said conical configuration preventing the dental anchor from moving transversely out of said passageway means when the dental anchor extends through said front end portion.

16. A combination according to claim 11, wherein said engageable means includes a square shaped section on said rear end portion.

17. A combination according to claim 11 including a manual holder for manual rotation of said body member, said manual holder being provided with means for engageably receiving said engageable means of said rear end portion.

18. A combination according to claim 17, wherein said manual holder is provided with pin means for advancing said torque transferring portion of the dental anchor to said notch means.

19. A combination according to claim 11 including a handpiece holder for power rotation of said body member by a dental handpiece, said handpiece holder being provided with means for engageably receiving said engageable means of said rear end portion.

20. A combination according to claim 19, wherein said handpiece holder is provided with pin means for advancing said torque transferring portion of the dental anchor to said notch means.

* * * * *